United States Patent [19]
Bzoch

[11] Patent Number: 5,895,366
[45] Date of Patent: Apr. 20, 1999

[54] HIP AND KNEE ABDUCTOR WITH AIR BLADDER

[75] Inventor: Jan J. Bzoch, South Pasadena, Fla.

[73] Assignee: Orthosis Corrective Systems Corp., Pinellas Park, Fla.

[21] Appl. No.: 08/662,788

[22] Filed: Jun. 12, 1996

[51] Int. Cl.$^6$ ........................................... A61F 5/00
[52] U.S. Cl. ................. 602/24; 602/13; 128/845; 128/DIG. 20
[58] Field of Search .................. 602/5, 13, 23, 602/24; 128/845, 846, 882, DIG. 20

[56] References Cited

U.S. PATENT DOCUMENTS

| | | | |
|---|---|---|---|
| 5,040,525 | 8/1991 | Georgijevic | 602/23 |
| 5,123,407 | 6/1992 | Dewhurst | 602/13 X |
| 5,201,761 | 4/1993 | Serola | 128/845 X |
| 5,259,397 | 11/1993 | McCabe | 128/882 X |
| 5,362,305 | 11/1994 | Vam | 602/24 |
| 5,418,991 | 5/1995 | Shiflett | 602/24 X |
| 5,558,628 | 9/1996 | Bzoch | 602/24 |
| 5,681,270 | 10/1997 | Klearman et al. | 602/23 X |

OTHER PUBLICATIONS

L'nard Restorative Concepts, Inc., L'nard Hip And Knee Abductor, 2 pages.
MMAR Medical Group, Inc., M&M Variflex, 1 page.
Orthosis Corrective Systems, Inc., Oscar Hko, 2 pages.
Restorative Care of America, Inc., RCAI Hip And Knee Abductor, 3 pages.
Orthotic Rehab. Products, Inc., Vari–Duct Hip And Knee Orthosis, 3 pages.

*Primary Examiner*—Linda C. Dvorak
*Attorney, Agent, or Firm*—James E. Larson; Larson & Larson, P.A.

[57] ABSTRACT

A hip and knee abductor having a pair of leg securing members and a center pocket integrally attached therebetween. The center pocket receives an air inflation means capable of receiving, retaining and expelling air. The introduction of air in the air inflation means permits abduction of contracted legs. The unique use of the air inflation means permits the use of the abductor with fully contracted legs. A pair of rigid plates are inserted within retaining pockets formed in the pair of leg securing members for communicating with the expandable air inflation means and thereby applying lateral pressure to an inner portion of contracted legs.

9 Claims, 3 Drawing Sheets

HIP AND KNEE ABDUCTOR WITH AIR BLADDER

BACKGROUND OF THE INVENTION

1. Field of the Invention

This invention relates to hip and knee orthosis devices. More particularly, it relates to a hip and knee abductor having an inflatable air bladder.

2. Description of Prior Art

Hip and knee orthosis devices are known in the prior art. Traditionally, they were used to stabilize the hip and knees of a patient who had experienced trauma to the lower portion of the body. Many of the prior art devices incorporated a pair of curved, rigid members for positioning juxtaposed to the inner thigh portion of the patient. A soft and pliable material is inserted over the rigid members for contact with the person's skin. A static center element is mounted between the rigid members retaining the patient's hip and knees in a stabilized position for treating hip and knee contractures and post operative lower extremity adduction.

In an effort to permit range of motion in a patient experiencing knee contractures and post operative lower extremity adduction, improvements in the above described device were developed. Such improvements enabled the orthosis to be adjusted permitting hip and knee abduction and range of motion to the affected joints. One example of such an improvement provided a center bar having a plurality of holes for receiving a spring loaded pin. The pin can be positioned in any one of the holes for providing different levels of abduction. Although the device has proven to be effective in providing different levels of abduction, the repositioning of the pin has proven to be awkward. In addition, the prior art devices can be difficult to insert between the contracted knees of a patient experiencing extreme contractures, such that a very small space remains between the two opposed inner lateral portions of a patient's contracted knees. Yet further, such prior art devices rely on predetermined positioning. A prior art device as described above does not allow for very small incremental changes to the positioning. Accordingly, a first position could be too small of an amount of abduction while a second adjacent position could be too much of an amount of abduction.

An improved hip and knee orthosis is needed, permitting knee and hip abduction and range of motion to the affected joints which does not utilized a center bar positioning portion and permits very minute incremental abduction changes.

SUMMARY OF THE INVENTION

I have developed an improved hip and knee orthosis for fast and easy use which does not utilize a center bar portion. Accordingly, many of the disadvantages experienced with orthosis devices in the prior art are eliminated.

My improved orthosis has a pair of leg securing members constructed of a soft fabric for securing around the thighs of a patient experiencing contractures of the legs and hips. A center pocket is integrally attached to the leg securing members and intermediately disposed between such two leg securing members. An inflatable bladder is inserted within the center pocket for inflation. A valve is provided in the inflatable bladder for the introduction and release of air. A pair of rigid plates, contoured to follow the shape of an inner thigh, are inserted within pockets of the leg securing members. Such rigid plates provide a means for applying lateral pressure against the inner thigh once the bladder is inflated.

Since there are no rigid center portions (ie. a center bar portion) positioned between the two leg securing members, my improved orthosis can be inserted between two completely contracted legs. Accordingly, my improved device allows range of motion treatment beginning at 0 degrees. Upon inserting my improved device between the completely contracted legs, air is introduced within the air bladder permitting the legs to be abducted.

The device of the present invention can also be used below the knees of a patient. Accordingly, the device is applied to the patient such that the leg securing members are secured around the calves of the patient instead of the thighs. Yet further, my device can be used when a patient is vertically positioned. A pair of clips are attached near a top portion to the rigid plates and protrude through the soft fabric for engagement with a pair of straps which can be secured about the waist of the patient. This permits the device to remain on the patient if the patient is vertically situated.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

In referring to elements of the present invention and body parts of the patient in the following description it is understood that the left and right perspectives will be considered the perspective of the patient.

Figure 1:
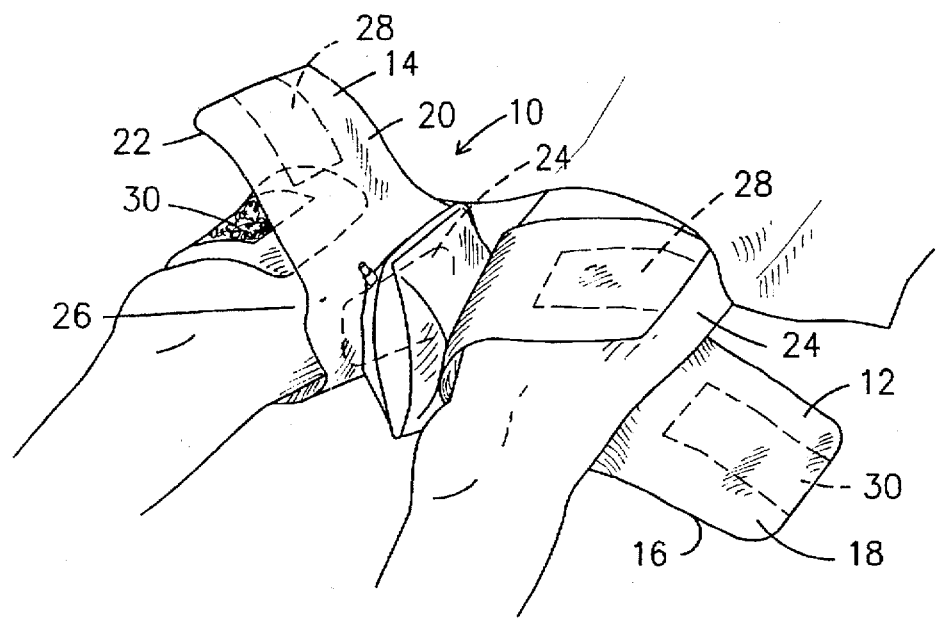
FIG. 1 is a perspective view of the hip and knee abductor of the present invention being applied to a patient.

Referring to FIG. 1, a hip and knee abductor 10 has a left and a right leg securing member 12 and 14 respectively. Left leg securing member 12 has a top and bottom surface 16 and 18 respectively. Right leg securing member 14 has a top and bottom surface 20 and 22 respectively. Abductor 10 is applied to a patient by wrapping left leg securing member 12 around a left thigh 24 of the patient and by wrapping right leg securing member 14 around a right thigh 26 of the patient such that bottom surface 18 of left leg securing member 12 contacts the skin of patient left thigh 24 and bottom surface 22 of right leg securing member 14 contacts the skin of patient right thigh 26.

Figure 2:
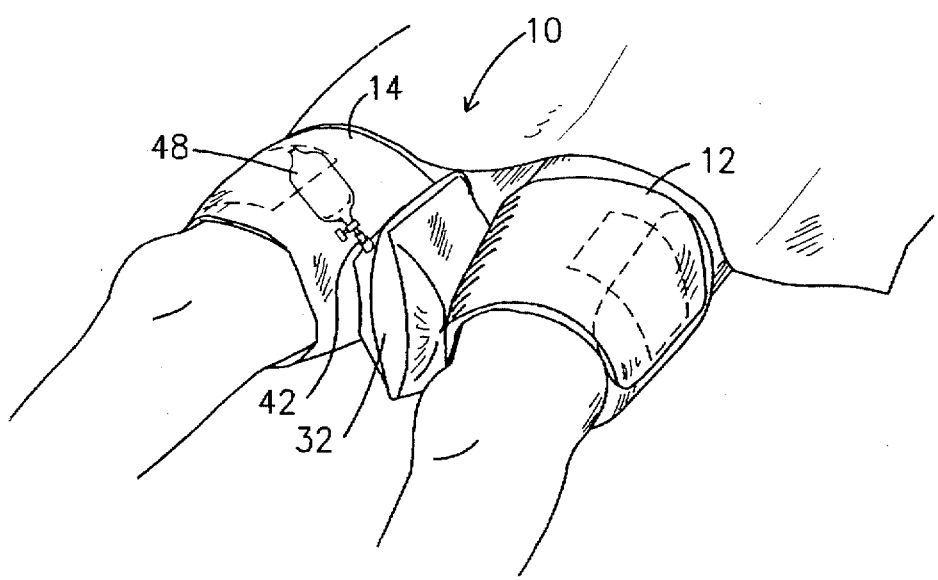
FIG. 2 is a perspective view of the hip and knee abductor fully applied to the patient.

Abductor 10 is secured to the patient by hook and loop material disposed upon the top and bottom surfaces of left and right leg securing member 12 and 14 respectively. As shown in FIG. 1, loop material 28 is stitched upon bottom surface 18 of left leg securing member 12 and hook material 30 is stitched upon top surface 16 of left leg securing member 12. Likewise, loop material 28 is stitched upon bottom surface 22 of right leg securing member 14 and hook material 30 is stitched upon top surface 20 of right leg securing member 14. When the corresponding hook and loop material engage one another on each respective leg securing member, abductor 10 is fully applied to the patient, as shown in FIG. 2.

Figure 4:
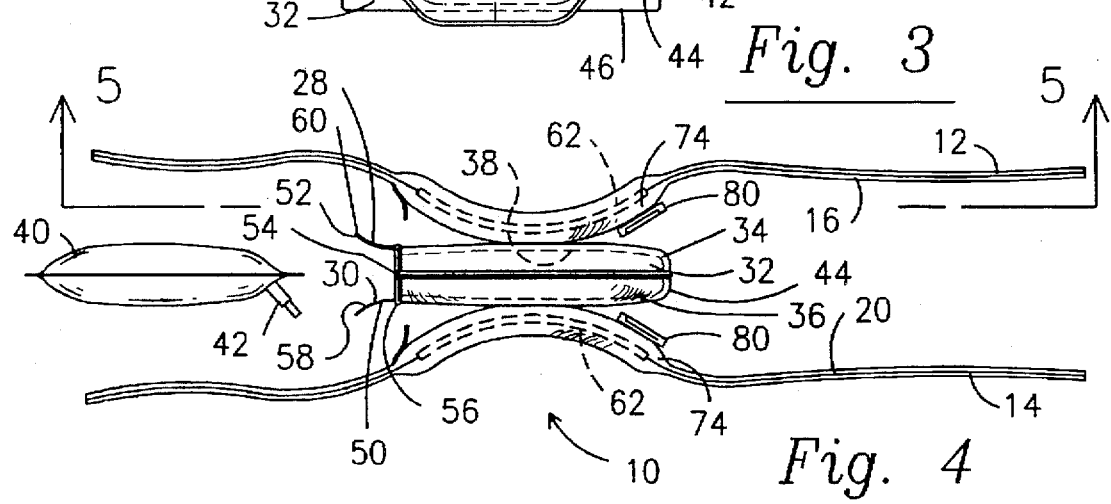
FIG. 4 is a top plan view of the hip and knee abductor showing how an air bladder is insertable within a center pocket of the abductor.

As shown in FIG. 4, a center pocket member 32 is disposed intermediate left and right leg securing members 12 and 14. Center pocket member 32 has a left and right outer surface 34 and 36 respectively and an inner cavity 38. Center pocket member 32 is integrally attached to left and right leg securing members 12 and 14 forming abductor 10. Particularly, left outer surface 34 of center pocket member 32 is stitched to top surface 16 of left leg securing member 12. Further, right outer surface 36 of center pocket member 32 is stitched to top surface 20 of right leg securing member 14. Any pattern of stitching that adequately secures center pocket member 32 to left and right leg securing members 12 and 14 can be used. In the preferred embodiment of the present invention, a rectangular shaped stitching pattern (not shown) is used to secure center pocket member 32 to left and right leg securing members 12 and 14 respectively.

Referring to FIG. 4, an inflatable air bladder 40 is insertable within inner cavity 38 of center pocket member 32. Air bladder 40 has a valve 42 disposed along a bottom edge 46 (see FIG. 3) permitting ingress and egress of air. A small aperture 44 formed through right outer surface 36 of center pocket member 32 along bottom edge 46 of center pocket member 32 permits valve 42 to protrude through center pocket member 32. Referring to FIG. 2, a ball pump 48 attaches to valve 42 for introducing and expelling air in and out of the air bladder inserted within center pocket 32. Once abductor 10 is fully applied to a patient, as illustrated in FIG. 2, air may be introduced into the air bladder inserted within center pocket 32 for the purpose of spreading the hip and knee of a patient within a range of 0 to 30°. The unique abductor of the present invention and the use of the air bladder permits applying abductor 10 to fully contracted hips and knees of patients representing range of motion exercise beginning at 0 degrees.

Referring to FIG. 4, a first and second flap 50 and 52 are integrally attached to at an open end 54 of center pocket member 32. In the preferred embodiment, flaps 50 and 52 are sewn to opposed horizontal edges 56 of center pocket member 32, although alternate means of attaching flaps 50 and 52 to center pocket member 32 could be used. Flaps 50 and 52 utilize hook and loop material for securing to one another and for effectively closing open end 54 of center pocket member 32 thereby retaining air bladder 40 in inner cavity 38 of center pocket member 32. It is understood that alternate means of securing could be employed to effectively close open end 54 of center pocket member 32. Such alternate means include, but are not limited to, using either a metal teeth or a groove and channel zipper, a button or snap mechanism or a fold over flap. In the preferred embodiment, hook material 30 is disposed upon an inner surface 58 of first flap 50 and loop material 28 is disposed upon an outer surface 60 of second flap 52.

To permit secure and comfortable fitting of abductor 10 to the thighs 24 and 26 of a patient, a rigid plate 62 is mounted within each leg securing member 12 and 14 (see FIGS. 3, 4, 5 and 8). In addition, rigid plate 62 applies lateral pressure to the inner thigh area of each patient thigh 24 and 26 as air bladder 40 is inflated. This lateral pressure permits abduction of the patient contracted hips and knees.

Figure 3:
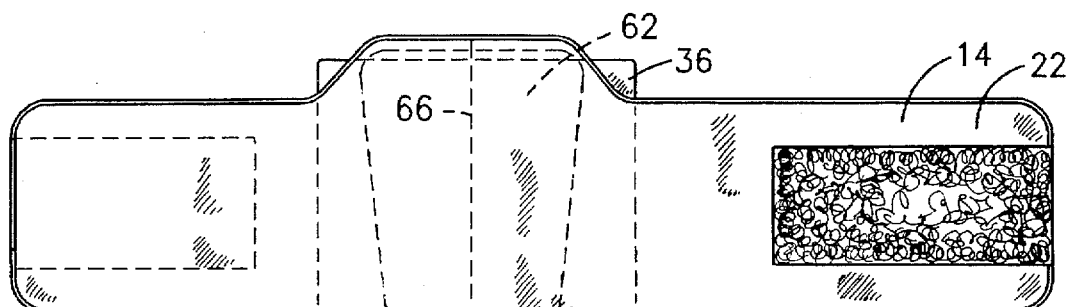
FIG. 3 is a right side elevational view of the hip and knee abductor showing a bottom surface of a right leg securing member.
Figure 6:
FIG. 6 is a top plan view of a plate insertable within a leg securing member pocket.
Figure 7:
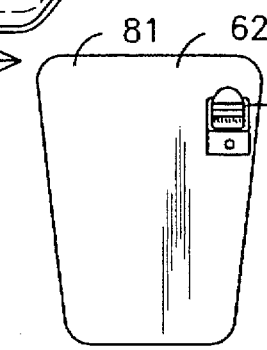
FIG. 7 is a front elevational view of the plate.

Referring to FIG. 7, a side elevational view shows a rigid plate 62 used in the present invention. The shaped illustrated in FIG. 7 is the preferred shape used in the present invention, although it is understood that changes to the shape of rigid plate can be made to accomplish other desired abduction of contracted hips and knees. Referring to FIG. 6, a top plan view of rigid plate 62 is illustrated to show how the contoured shape generally follows the shape of the inner thigh of a person. Again, it is understood that the shape depicted in FIG. 6, is the preferred shape, although changes in the contour could be made to accommodate fitting abductor 10 to thighs of varying shape. Referring to FIG. 3, an axial seam 66 is stitched in bottom surface 22 of right leg securing member 14. An identical seam is stitched in bottom surface 18 of left leg securing member 12 (not shown). Axial seam 66 permits left and right leg securing members 12 and 14 respectively to generally conform to the contour of rigid plate 62 when juxtaposed to a patient thigh.

Figure 5:
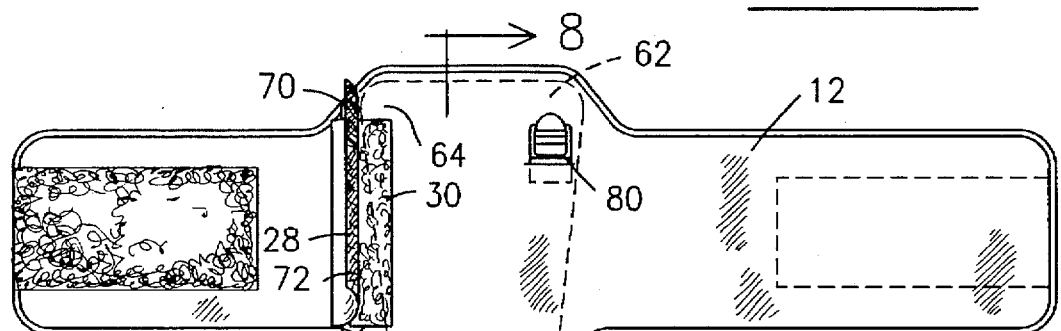
FIG. 5 is a cross-sectional view along lines 5—5 of FIG. 4 showing a top side of a left leg securing member.
Figure 9:
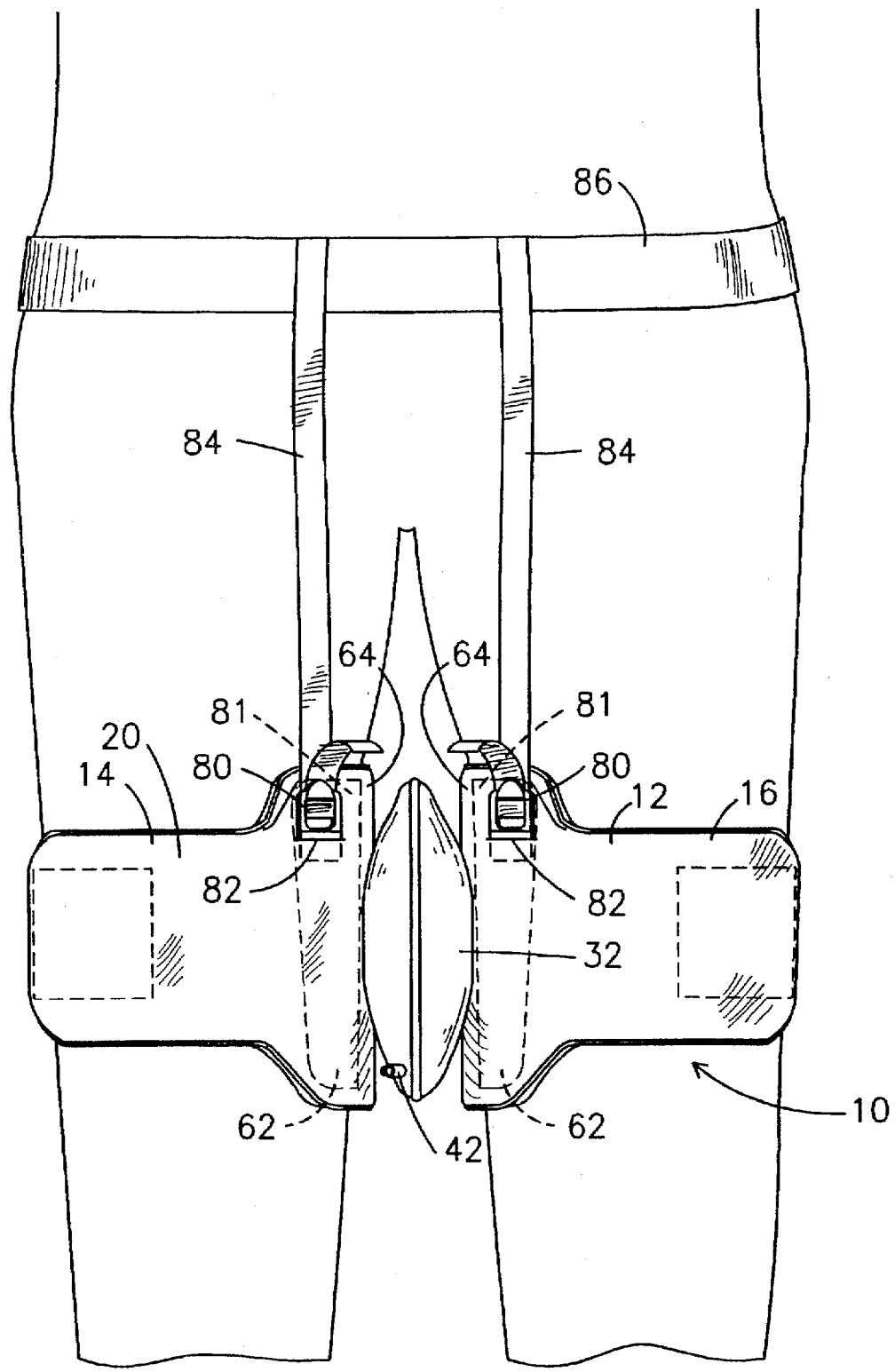
FIG. 9 is a front elevational view of the hip and knee abductor fully applied to a patient and employing an optional removable securing means.

Referring to FIG. 5, rigid plate 62 is inserted within a leg securing member pocket 64 of left and right leg securing member 12 and 14 respectively. It is noted that FIG. 5 is representative of left leg securing member 12, but the configuration of each rigid plate 62 within each leg securing member pocket 64 is identical on each of the leg securing members 12 and 14 respectively. That is, a leg securing member pocket 64 is formed in top surface 16 and 18 respectively of left and right leg securing member 12 and 14. Referring to FIG. 9, it is shown (by hidden lines) how a pair of rigid plates 62 are inserted within the leg securing member pockets 64 on left and right leg securing member 12 and 14 respectively.

Referring to FIG. 5, an opening 68 is formed in leg securing member pocket 64 permitting rigid plate 62 to be inserted therein. Again, the configuration of opening 68 formed in leg securing member pocket 64 is identical on both leg securing members 12 and 14 respectively, even though FIG. 5 is representing left leg securing member 12. A closure flap 70 is integrally attached to opening 68 and has a closure means disposed thereon. In the preferred embodiment hook and loop material is used as the closure means. Specifically, hook material 30 is integrally attached by stitching to the top surface of the respective leg securing member and proximal to opening 68. Loop material 28 is disposed along a bottom surface 72 of closure flap for engagement with hook material 30. Closure of opening 68 retains rigid plate 62 within leg securing member pocket 64.

Figure 8:
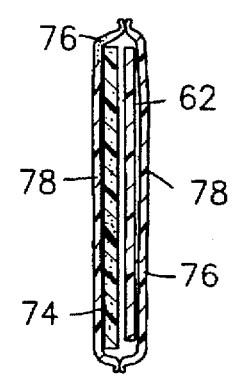
FIG. 8 is a cross-sectional view along lines 8—8 of FIG. 5 showing the insertable plate juxtaposed to a layer of foam within a leg securing member pocket.

Referring to FIGS. 4 and 8, a foam layer insert 74 is inserted intermediate the bottom surfaces of the leg securing members and the rigid plate 62. Foam layer 74 adds additional comfort to the patient when abductor 10 is applied to a patient and during actual abduction procedures. Foam layer insert 74 is retained within leg securing member pocket 64 by the stitching of axial seam 66.

Top and bottom surfaces of leg securing members 12 and 14 are each constructed of two sheets of soft fabric generally known as "headliner" and have an intermediate layer of soft foam 78 disposed between the two sheets of the "headliner". Referring to FIG. 8, a cross sectional view shows the two sheets of "headliner" 76 surrounding the soft layer of foam 78. In addition, FIG. 8 shows foam layer insert 74 positioned intermediate rigid plate 62 and bottom surface 18 of left leg securing member 12.

In the preferred embodiment, the layer of soft foam 78 disposed between the two sheets of "headliner" is sold by EASTMAN KODAK COMPANY under the trademark "KODEL". The rigid plate 62 is made from a hard polymer, although aluminum or stainless steel could be employed.

Referring to FIG. 9, a pair of clips 80, one each integrally attached to each rigid plate 62 at each top end 81 of each rigid plate 62 (see also FIG. 7), protrude through top surfaces 16 and 20 of left and right leg securing members 12 and 14 respectively. A pair of small slits 82 are formed in top surfaces 16 and 20 respectively of left and right leg securing members 12 and 14 permitting clips 80 to protrude therethrough. Clips 80 are provided for engagement with a pair of straps 84 which secure around the body of the patient by a belt portion 86. In the preferred embodiment, straps 84 engage with a waist belt providing an additional means for securing abductor 10 to the patient. An alternate set of straps could be used to secure around the shoulders of a patient instead of the waist. As shown in FIG. 9, the strap configuration allows the patient to be positioned vertically without abductor 10 slipping from the applied position. In addition, although not shown, abductor 10 can be applied around the calves portion of the patient. In this application, abductor 10 can be used with or without the strap configuration depending on whether the patient will be vertically positioned. Further, with the straps loosened or disengaged, abductor 10 can be moved up from the calve position to the thigh position without abductor 10 being removed from the patient. It is noted that the unique configuration of abductor 10 allows this sliding of abductor 10 about the legs of the patient even if the knees and or hips are fully adducted. Depending on the amount of adduction, the operator can merely removed some of the air from the air bladder prior to sliding the abductor 10 up from the calve to the thigh position.

Equivalent elements can be substituted for the ones set forth above to achieve the same results in the same manner.

Having thus described the invention what is claimed and desired to be secured by Letters Patent is:

1. A hip and knee abductor for applying to the contracted legs of a patient, the abductor comprising:

a left leg securing member having opposed first and second ends and a top and bottom surface, a right leg securing member having opposed first and second ends and a top and bottom surface, the left and right leg securing members for wrapping, respectively, around the left and right legs of a patient, a piece of loop material stitched upon each of the left and right leg securing member bottom surfaces and a piece of hook material stitched upon each of the left and right leg securing member top surfaces, each piece of hook material stitched upon each of the left and right leg securing member capable of engaging the respective piece of loop material stitched upon each of the left and right leg securing member, a left and right leg securing member pocket, the left leg securing member pocket formed at a center portion in the left leg securing member top surface and the right leg member securing pocket formed at a center portion in the right leg securing member top surface, the left and right leg securing member pocket each having an opening and a closure flap, a left and right rigid plate, the left rigid plate insertable within the left leg securing member pocket through the left leg securing member pocket opening and the right rigid plate insertable within the right leg securing member pocket through the right leg securing member pocket opening, the closure flap of each of the left and right leg securing member pockets capable of securing the respective rigid plate within the respective leg securing pocket, and air inflation means for permitting the patient legs to be abducted, the air inflation means attached to the left and right leg securing members intermediately disposed therebetween.

2. The hip and knee abductor according to claim 1, wherein the left and right rigid plates have a concave shape permitting the left and right rigid plates to fit comfortably against an inner portion of a patient thigh or calf.

3. The hip and knee abductor according to claim 1, wherein the air inflation means is an inflatable bladder having a valve, the inflatable bladder capable of receiving, retaining and expelling air through the valve, the inflatable bladder expanding when receiving air thereby applying outwardly directed pressure in communication with the left and right rigid plates for abducting the contracted legs of the patient.

4. The hip and knee abductor according to claim 3, further comprising:

a center pocket member having a left and right outer surface, an open end and an aperture formed along a bottom edge of the right outer surface, the left and right outer surface defining an inner cavity, the inflatable bladder insertable within the inner cavity through the open end such that the air bladder valve protrudes through the center pocket member aperture, the left outer surface integrally attached to the left leg securing member top surface at the left leg securing member center portion, the right outer surface integrally attached to the right leg securing member top surface at the right leg securing member center portion.

5. The hip and knee abductor according to claim 4 wherein the left and right outer surfaces of the center pocket member are constructed of two sheets of soft fabric and a layer of foam disposed therebetween.

6. The hip and knee abductor according to claim 1, further comprising:

a left slit formed in the left leg securing pocket, a right slit formed in the right leg securing pocket, a left clip integrally attached to the left rigid plate such that when the left rigid plate is inserted within the left leg securing member pocket the left clip protrudes through the left slit, a right clip integrally attached to the right rigid plate such that when the right rigid plate is inserted within the right leg securing member pocket the right clip protrudes through the right slit, a pair of straps connectable to a belt and engageable with the left and right clips for retaining the abductor upon the patient, a left and right foam pad insertable within the left and right leg securing member pockets such that the left and right foam pads are respectively positioned between the left and right rigid plates and the bottom surfaces of the left and right leg securing members, and a left and right axial seam, the left axial seam stitched in the left leg securing member bottom surface and the right axial seam stitched in the right leg securing member, the left and right axial seams retaining the left and right foam pads within the left and right leg securing member pockets respectively and assisting the left and right leg securing members to wrap around the respective patient leg.

7. The hip and knee abductor according to claim 1, wherein contracted legs can be spread within a range of motion of 0 to 30 degrees.

8. The hip and knee abductor according to claim 1, wherein the top and bottom surfaces of the left and right leg securing members are each constructed of two sheets of soft fabric and a layer of foam disposed therebetween.

9. The hip and knee abductor of claim 8 wherein the fabric is headliner.

* * * * *